United States Patent
Onishi

(10) Patent No.: US 7,113,629 B2
(45) Date of Patent: Sep. 26, 2006

(54) PATTERN INSPECTING APPARATUS AND METHOD

(75) Inventor: Hiroyuki Onishi, Kyoto (JP)

(73) Assignee: Dainippon Screen Mfg. Co., Ltd., Kyoto (JP)

( * ) Notice: Subject to any disclaimer, the term of this patent is extended or adjusted under 35 U.S.C. 154(b) by 653 days.

(21) Appl. No.: 10/109,869

(22) Filed: Apr. 1, 2002

(65) Prior Publication Data

US 2002/0150286 A1 Oct. 17, 2002

(30) Foreign Application Priority Data

Apr. 11, 2001 (JP) ............................. 2001-112538
Apr. 11, 2001 (JP) ............................. 2001-112539

(51) Int. Cl.
*G06K 9/00* (2006.01)
(52) U.S. Cl. ...................... 382/149; 382/141; 382/145; 382/147; 382/151; 348/87; 348/126
(58) Field of Classification Search ................ 382/141, 382/145, 147, 149, 151; 348/86, 87, 125, 348/126, 129; 702/35, 36; 356/237.1, 237.2, 356/237.5, 394; 700/110; 250/559.4, 559.41, 250/559.42, 559.43, 559.44, 559.45
See application file for complete search history.

(56) References Cited

U.S. PATENT DOCUMENTS 5,153,444 A * 10/1992 Maeda et al. .......... 250/559.05
5,173,719 A * 12/1992 Taniguchi et al. ........... 356/394
5,185,812 A * 2/1993 Yamashita et al. .......... 382/145
6,140,140 A * 10/2000 Hopper ........................... 438/8
6,236,057 B1 * 5/2001 Shishido et al. ........ 250/559.45

FOREIGN PATENT DOCUMENTS

| JP | 04-279041 | 10/1992 |
|---|---|---|
| JP | 6-56293 | 7/1994 |
| JP | 08-320294 | 12/1996 |
| JP | 11-194099 | 7/1999 |
| JP | 2976550 | 9/1999 |
| JP | 2000-049203 A | 2/2000 |
| JP | 3187827 | 5/2001 |

* cited by examiner

*Primary Examiner*—Bhavesh M. Mehta
*Assistant Examiner*—John Strege
(74) *Attorney, Agent, or Firm*—McDermott Will & Emery LLP

(57) ABSTRACT

A pattern inspecting apparatus includes a substrate support table, a table driver for driving the substrate support table through actuators, a camera, an image processor, and a controller connected to a keyboard and a CRT. The image processor has a chip comparing inspection unit for executing a chip comparing inspection, a cell comparing inspection unit for executing a cell comparing inspection, an image memory, an integrating decision unit for integrating results of inspection by the chip comparing inspection unit and results of inspection by the cell comparing inspection unit and making a final decision as to the presence of a defect, and an area memory.

8 Claims, 15 Drawing Sheets

FIG. 3

```
0 0 0 0 0 0 0 0 0 0 0 0 0 0 0      0 0 0 0 0 0 0 0 0 0 0 0 0 0 0
0 0 0 0 0 1 1 1 1 1 1 1 1 1 0      0 1 1 1 1 0 0 0 0 0 0 0 0 0 0
0 0 0 0 0 1 1 1 1 1 1 1 1 1 0      0 1 1 1 1 0 0 0 0 0 0 0 0 0 0
0 0 0 0 0 1 1 1 1 1 1 1 1 1 0      0 1 1 1 1 0 0 0 0 0 0 0 0 0 0
0 0 0 0 0 1 1 1 1 1 1 1 1 1 0      0 1 1 1 1 0 0 0 0 0 0 0 0 0 0
0 0 0 0 0 0 0 0 0 0 0 0 0 0 0      0 1 1 1 1 0 0 0 0 0 0 0 0 0 0
0 0 0 0 0 1 1 1 1 1 1 1 1 1 0      0 1 1 1 1 0 0 0 0 0 0 0 0 0 0
0 0 0 0 0 1 1 1 1 1 1 1 1 1 0      0 1 1 1 1 0 0 0 0 0 0 0 0 0 0
0 0 0 0 0 1 1 1 1 1 1 1 1 1 0      0 1 1 1 1 0 0 0 0 0 0 0 0 0 0
0 0 0 0 0 1 1 1 1 1 1 1 1 1 0      0 1 1 1 1 0 0 0 0 0 0 0 0 0 0
0 0 0 0 0 0 0 0 0 0 0 0 0 0 0      0 0 0 0 0 0 0 0 0 0 0 0 0 0 0
``` areas for                area for
cell comparing inspection   chip comparing inspection

FIG. 4

```
0 0 0 0 0 0 0 0 0 0 0 0 0 0 0      0 0 0 0 0 0 0 0 0 0 0 0 0 0 0
0 0 0 0 0 0 1 1 1 1 1 1 1 1 0      0 1 1 1 1 0 1 1 1 1 1 1 1 1 0
0 0 0 0 0 0 1 1 1 1 1 1 1 1 0      0 1 1 1 1 0 1 1 1 1 1 1 1 1 0
0 0 0 0 0 0 1 1 1 1 1 1 1 1 0      0 1 1 1 1 0 1 1 1 1 1 1 1 1 0
0 0 0 0 0 0 1 1 1 1 1 1 1 1 0      0 1 1 1 1 0 1 1 1 1 1 1 1 1 0
0 0 0 0 0 0 1 1 1 1 1 1 1 1 0      0 1 1 1 1 0 1 1 1 1 1 1 1 1 0
0 0 0 0 0 0 0 0 0 0 0 0 0 0 0      0 1 1 1 1 0 0 0 0 0 0 0 0 0 0
0 0 0 0 0 0 1 1 1 1 1 1 1 1 0      0 1 1 1 1 0 1 1 1 1 1 1 1 1 0
0 0 0 0 0 0 1 1 1 1 1 1 1 1 0      0 1 1 1 1 0 1 1 1 1 1 1 1 1 0
0 0 0 0 0 0 1 1 1 1 1 1 1 1 0      0 1 1 1 1 0 1 1 1 1 1 1 1 1 0
0 0 0 0 0 0 1 1 1 1 1 1 1 1 0      0 1 1 1 1 0 1 1 1 1 1 1 1 1 0
0 0 0 0 0 0 0 0 0 0 0 0 0 0 0      0 0 0 0 0 0 0 0 0 0 0 0 0 0 0
``` areas for              areas for
cell comparing inspection   chip comparing inspection FIG. 7
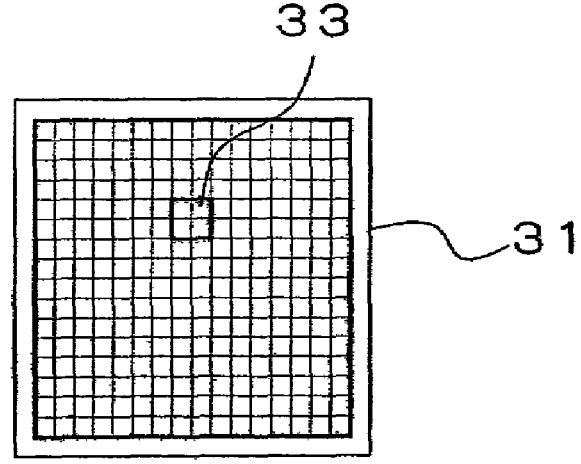
(a)
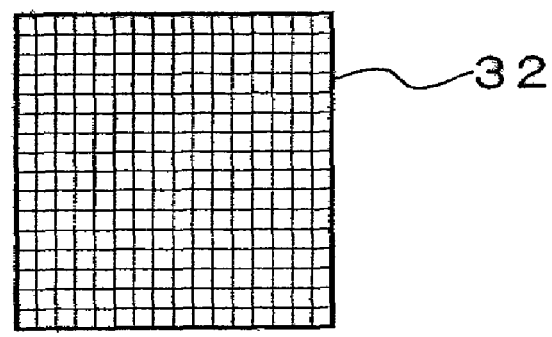
(b)

F I G. 8
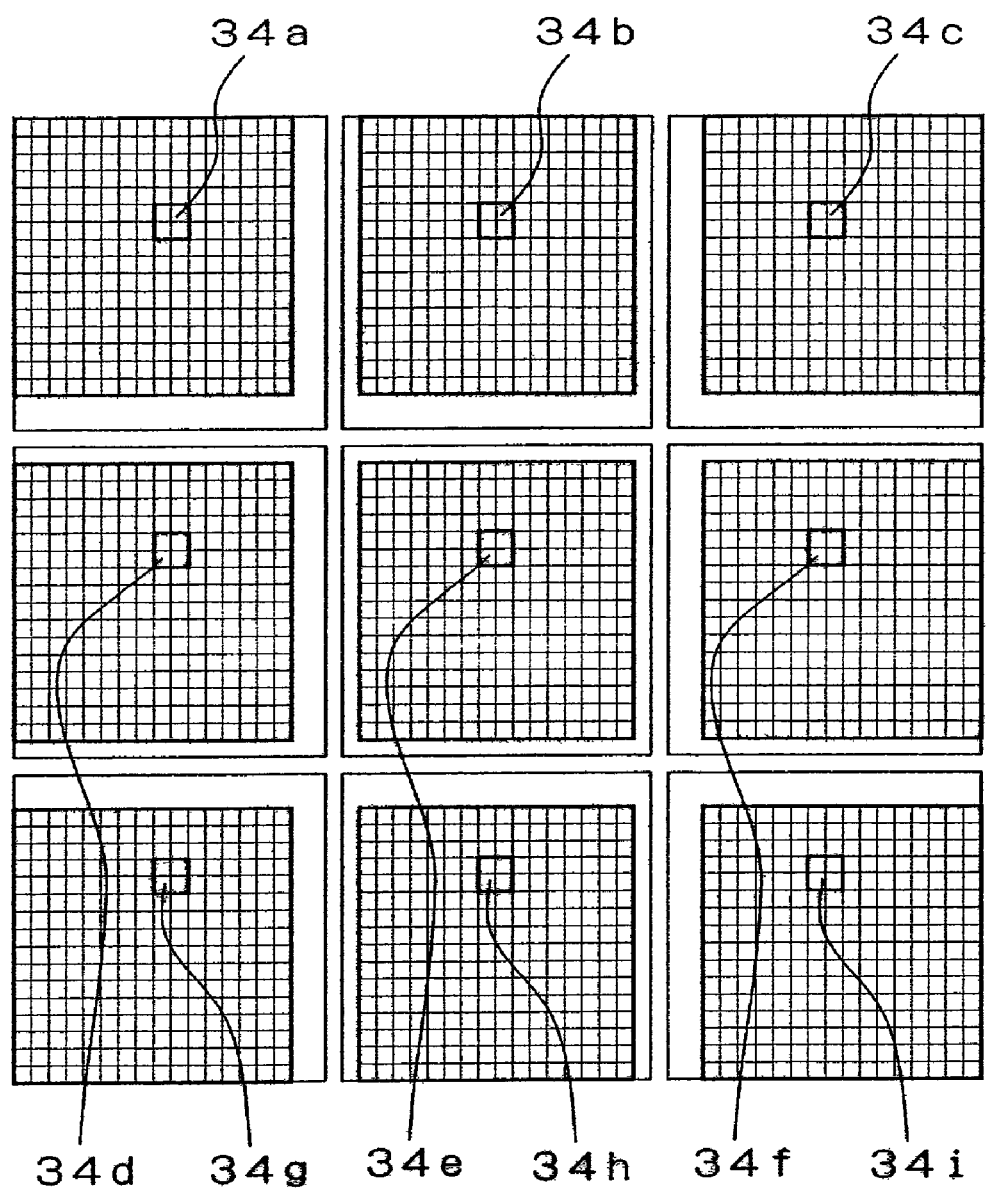

F I G. 1 0
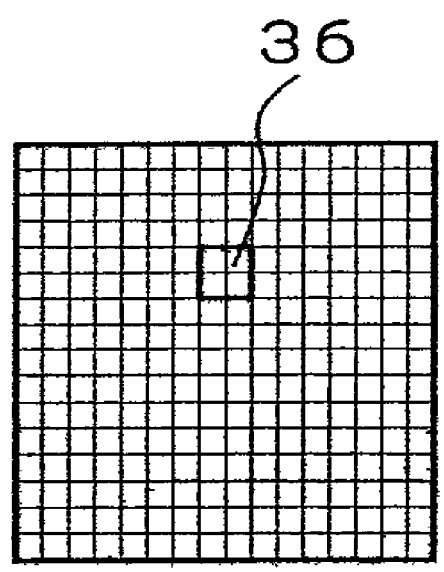

FIG. 11
(a)
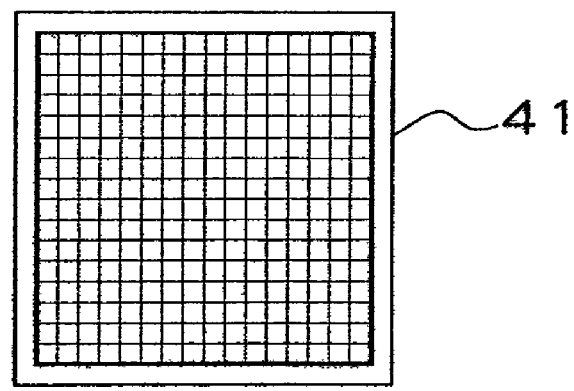
(b)
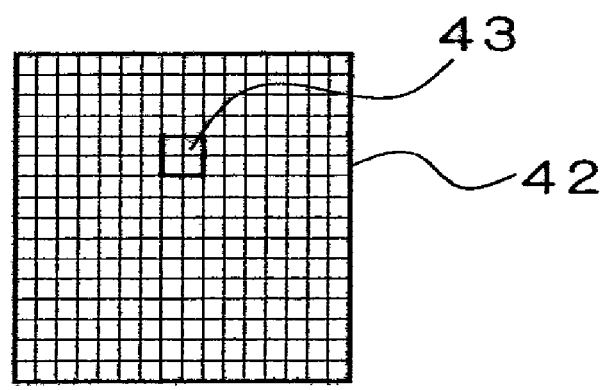

F I G. 1 6
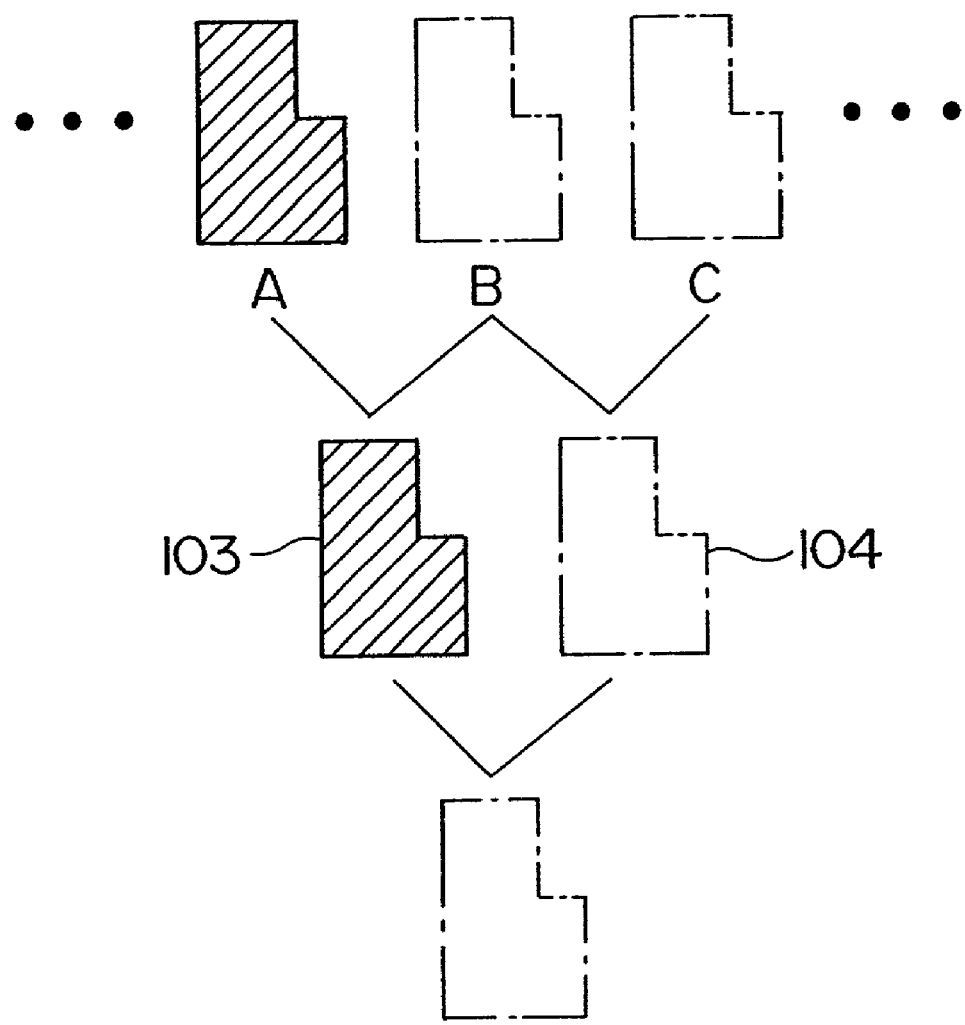

PATTERN INSPECTING APPARATUS AND METHOD

BACKGROUND OF THE INVENTION

1. Field of the Invention

The present invention relates to a pattern inspecting apparatus and method for inspecting patterns in numerous chips formed on substrates such as semiconductor wafers.

2. Description of the Related Art

Numerous chips formed on a semiconductor wafer include repetitive pattern areas having the same pattern formed repeatedly, such as charge storage portions of memory, and random pattern areas having other patterns formed therein. In inspecting such patterns in the chips, different inspecting methods are used for the repetitive pattern areas and random pattern areas.

That is, for the random pattern areas, a chip comparing inspection is employed to detect pattern defects by comparing corresponding patterns in a plurality of adjoining or adjacent chips. This chip comparing inspection is an inspecting method also called a die comparing inspection or random comparing inspection. The chip comparing inspection compares and inspects patterns arranged in two relatively remote locations on a semiconductor wafer, and therefore needs a relatively large error allowance.

For the repetitive pattern areas, a cell comparing inspection is employed to detect pattern defects by comparing adjoining or adjacent repetitive patterns in the same chip (see Japanese Patent Publication (Examined) No. 1994-56293). This cell comparing inspection is an inspecting method also called an array comparing inspection. The cell comparing inspection compares patterns lying close to each other, and therefore is capable of a highly accurate inspection.

Thus, in inspecting the patterns in both of the repetitive pattern areas and random pattern areas in chips formed on a semiconductor wafer, two types of pattern inspecting apparatus are used, one performing the die comparing inspection, and the other the cell comparing inspection. Alternatively, an inspecting apparatus operable in two detecting modes for the die comparing inspection and cell comparing inspection may be used to perform inspections for the repetitive pattern areas and random pattern areas by switching between the two modes.

Japanese Patent No. 2976550 discloses a pattern defect inspecting method which compares cells based on images taken of chips. Cell comparable portions and cell incomparable portions are set to the image areas. A cell comparing inspection is carried out for the cell comparable portions, while a chip comparing inspection is carried out for the cell incomparable portions.

FIG. 15 is an explanatory view illustrating an operation for detecting a defect by using the cell comparing inspection.

The cell comparing inspection compares repetitive pattern A and repetitive pattern B, and compares repetitive pattern B and repetitive pattern C. An AND operation is carried out on a result of comparison 101 between repetitive pattern A and repetitive pattern B, and a result of comparison 102 between repetitive pattern B and repetitive pattern C, thereby to detect a defect 100 inherent in repetitive pattern B.

This cell comparing inspection provides highly accurate results for minute defects formed in repetitive patterns, but cannot detect defects occurring over two or more cycles of pattern repetition.

Assume that, as shown in FIG. 16, both repetitive pattern B and repetitive pattern C are defective with a relatively large particle present on these patterns. In this case, an AND operation on a result of comparison 103 between repetitive pattern A and repetitive pattern B, and a result of comparison 104 between repetitive pattern B and repetitive pattern C would result in a finding that no defect is present in repetitive pattern B.

Thus, the cell comparing inspection will fail to detect a relatively large defect occurring over two or more cycles of pattern repetition as shown in FIG. 16.

Such a problem is a phenomenon occurring also with the pattern defect inspecting method described in U.S. Pat. No. 2,976,550 noted above. With the method described in U.S. Pat. No. 2,976,550, a relatively large defect present over two or more cycles of pattern repetition when setting cell comparable portions and cell incomparable portions will be recognized as a cell comparable portion. In time of cell comparing inspection, the relatively large defect present over two or more cycles of pattern repetition will result in a finding that no defect is present.

SUMMARY OF THE INVENTION

The object of this invention, therefore, is to provide a pattern inspecting apparatus and method for accurately detecting a relatively large defect occurring in repetitive pattern areas.

The above object is fulfilled, according to the present invention, by a pattern inspecting apparatus for inspecting patterns in numerous chips formed on a substrate, comprising a substrate support for supporting the substrate, a camera for acquiring images of the chips, a moving device for moving the substrate support and the camera relative to each other, an image memory for storing the images of the chips acquired by the camera, an area setting mechanism for setting a repetitive pattern area having repetitive patterns formed therein, and a random pattern area having random patterns formed therein, to each of the chips whose images are acquired by the camera, an area memory for storing the repetitive pattern area and the random pattern area, a cell comparing inspection unit for executing a cell comparison to detect a pattern defect by comparing the repetitive patterns in the repetitive pattern area set to each of the chips and stored in the area memory, and a chip comparing inspection unit for executing a chip comparison to detect a pattern defect by comparing corresponding patterns in the repetitive pattern area and the random pattern area set to the chips and stored in the area memory.

This pattern inspecting apparatus performs both the cell comparison and chip comparison for the repetitive pattern area, and the chip comparison for the random pattern area. In inspecting for defects in the repetitive pattern area and random pattern area, a relatively large defect occurring in the repetitive pattern area may be detected accurately.

In another aspect of the invention an inspecting apparatus for inspecting repetitive patterns in repetitive pattern areas of numerous chips formed on a substrate is characterized in that a pattern defect is detected by executing a cell comparison for comparing the repetitive patterns in each of the repetitive pattern areas of the chips, and a chip comparison for comparing corresponding patterns in the repetitive pattern areas of the chips.

This pattern inspecting apparatus detects a pattern defect by a cell comparison for comparing the repetitive patterns in each of the repetitive pattern areas of the chips, and a chip comparison for comparing corresponding patterns in the repetitive pattern areas of the chips. Thus, a relatively large defect occurring in a repetitive pattern area may be detected accurately.

In a further aspect of the invention, a pattern inspecting method is provided for inspecting patterns in numerous chips formed on a substrate. This method comprises an area setting step for setting a repetitive pattern area having repetitive patterns formed therein, and a random pattern area having random patterns formed therein to each of the chips, and a defect detecting step for executing both a cell comparison to detect a pattern defect by comparing the repetitive patterns in the repetitive pattern area set to each of the chips, and a chip comparison to detect a pattern defect by comparing corresponding patterns in the repetitive pattern area set to the chips, and executing the chip comparison to detect a pattern defect by comparing corresponding patterns in the random pattern area set to the chips. The area setting step may be executed for setting a repetitive pattern area having repetitive patterns formed therein, and a random pattern area having random patterns formed therein, by photographing the patterns on each of the chips, displaying the patterns in enlargement on a display device, and referring to the patterns displayed in enlargement.

With this pattern inspecting method, the patterns on each chip are photographed and displayed in enlargement on the display device. These patterns are used in setting a repetitive pattern area having repetitive patterns formed therein, and a random pattern area having random patterns formed therein. In this way, the repetitive pattern area and random pattern area are set with ease.

Other features and advantages of the present invention will be apparent from the following detailed description of the embodiments of the invention.

BRIEF DESCRIPTION OF THE DRAWINGS

For the purpose of illustrating the invention, there are shown in the drawings several forms which are presently preferred, it being understood, however, that the invention is not limited to the precise arrangement and instrumentalities shown.

FIG. 3 is an explanatory view showing an area for chip comparing inspection and areas for cell comparing inspection;

FIG. 4 is an explanatory view showing areas for chip comparing inspection and areas for cell comparing inspection;

FIG. 7 is a schematic view of a reference image and an image under inspection;

FIG. 8 is a schematic view of absolute value images;

FIG. 10 is a schematic view of a defect image;

FIG. 11 is a schematic view of a reference image and an image under inspection;

FIG. 16 is an explanatory view illustrating an operation for detecting a defect by using the cell comparing inspection.

DESCRIPTION OF THE PREFERRED EMBODIMENTS

Figure 1:
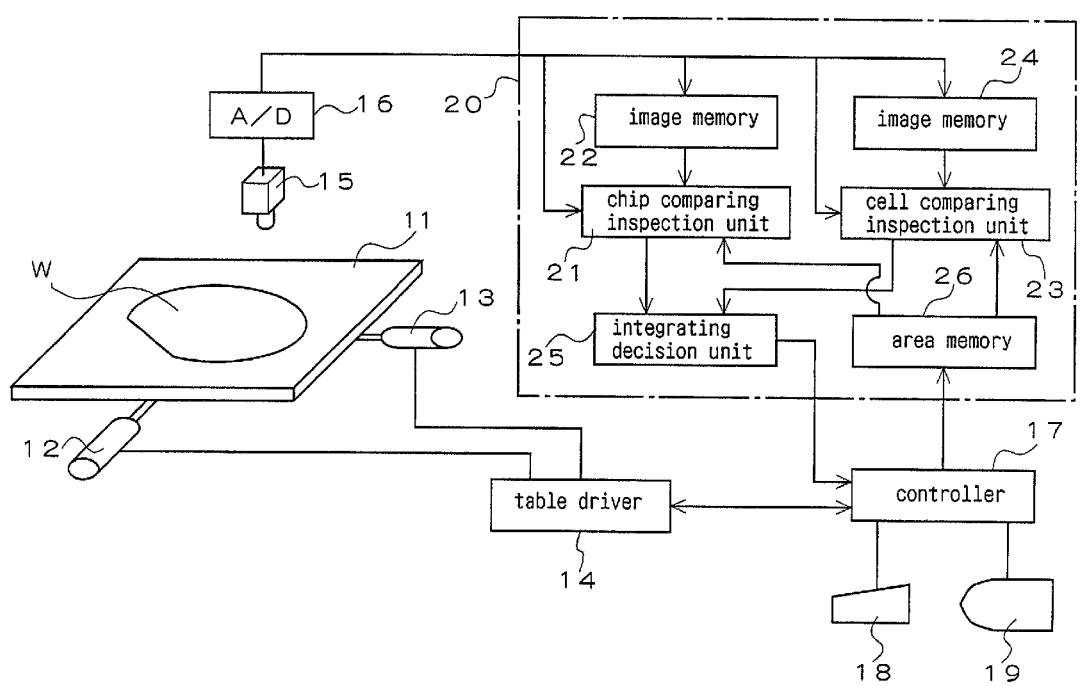
FIG. 1 is a schematic view of a pattern inspecting apparatus according to the present invention.

Embodiments of the present invention will be described hereinafter with reference to the drawings. FIG. 1 is a schematic view of a pattern inspecting apparatus according to the invention.

This pattern inspecting apparatus includes a substrate support table 11 for supporting a substrate, e.g. semiconductor wafer W, an actuator 12 for moving the substrate support table 11 in X-direction, an actuator 13 for moving the substrate support table 11 in Y-direction, a table driver 14 for driving the substrate support table 11 through the actuators 12 and 13, a camera 15 for photographing chips formed on the wafer W supported by the substrate support table 11, an image processor 20 to be described hereinafter, and a controller 17 for controlling the entire pattern inspecting apparatus. The controller 17 has, connected thereto, a keyboard 18 acting as an area setting device in time of area setting as described hereinafter, and a CRT 19 acting as an enlarged image display device.

The image processor 20 includes a chip comparing inspection unit 21 for performing a chip comparing inspection, an image memory 22 for temporarily storing images acquired through the camera 15 in time of chip comparing inspection, a cell comparing inspection unit 23 for performing a cell comparing inspection, an image memory 24 for temporarily storing images acquired through the camera 15 in time of cell comparing inspection, an integrating decision unit 25 for integrating results of inspection by the chip comparing inspection unit 21 and results of inspection by the cell comparing inspection unit 23 and making a final decision as to the presence of a defect, and an area memory 26 for storing repetitive pattern areas and random pattern areas set by using the keyboard 18 or the like. The chip comparing inspection unit 21, image memory 22, cell comparing inspection unit 23 and image memory 24 of the image processor 20 are connected to the camera 15 through an analog-to-digital converter 16.

Instead of separately providing the image memory 22 for temporarily storing images acquired through the camera 15 in time of chip comparing inspection and the image memory 24 for temporarily storing images acquired through the camera 15 in time of cell comparing inspection, a single image memory may be used for temporarily storing such images.

When inspecting patterns on the wafer W with the pattern inspecting apparatus having the above construction, an area setting step is executed first to set a repetitive pattern area having repetitive patterns formed therein, and a random pattern area having random patterns formed therein.

In this area setting step, the camera 15 is operated to photograph patterns on chips formed on the surface of wafer W. The image of the patterns on each chip is displayed in enlargement on the CRT 19.

Figure 2:
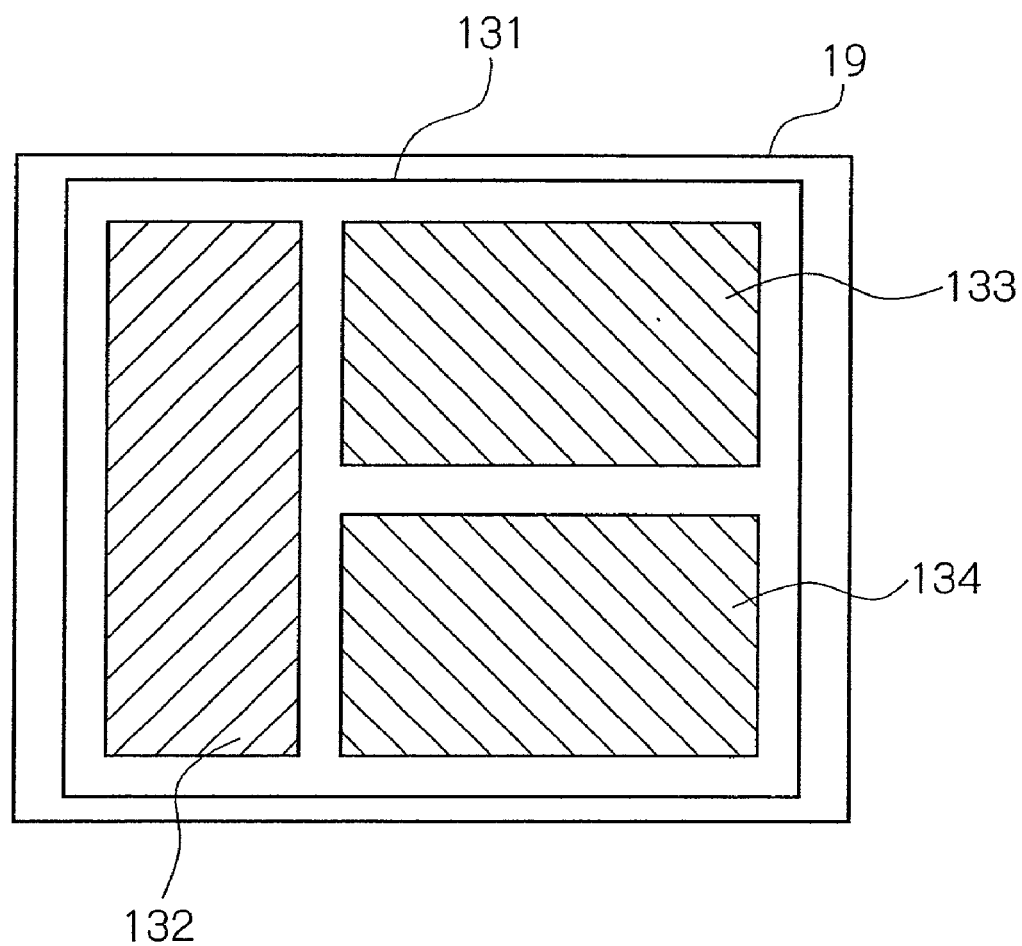
FIG. 2 is an explanatory view schematically showing an image of patterns on a chip displayed in enlargement on a CRT.

FIG. 2 is an explanatory view schematically showing an image of patterns on a chip 131 displayed in enlargement on the CRT 19.

In this embodiment, the chip 131 is assumed to include an area 132 having random patterns formed therein, and areas 133 and 134 having repetitive patterns formed therein.

Next, the operator, while observing the enlarged image displayed, sets these areas to be the random pattern area 132 having random patterns formed therein and the repetitive pattern areas 133 and 134 having repetitive patterns formed therein. In this area setting step, the operator sets the areas by using the keyboard 18 connected to the controller 17. The random pattern area 132 and repetitive pattern areas 133 and 134 set in the area setting step are stored in the area memory 26 of image processor 20.

This area setting step may be executed by the operator using the keyboard 18 or a mouse or the like not shown. Alternatively, the area setting step may be executed automatically by the controller 17, using a mode as described in Japanese Patent No. 2976550.

Based on the random pattern area 132 and repetitive pattern areas 133 and 134 stored in the area memory 26, it is determined which areas should be put to a chip comparing inspection and which area should be put to a cell comparing inspection. That is, as shown in FIG. 3, this inspecting mode determining step is executed, first, to set flags (numeral 1 in FIG. 3) signifying the chip comparing inspection for the random pattern area 132, and set flags (numeral 1 in FIG. 3) signifying the cell comparing inspection for the repetitive pattern areas 133 and 134. Then, as shown in FIG. 4, by copying the flags signifying the cell comparing inspection, flags signifying the chip comparing inspection are set to portions corresponding to the repetitive pattern areas 133 and 134. All this information is stored in the area memory 26 of image processor 20.

This inspecting mode determining step may be executed automatically by the controller 17, or by the operator using the keyboard 18 or the mouse or the like not shown.

The above step is followed by a pattern inspecting step. In this pattern inspecting step, the chip comparing inspection unit 21 and cell comparing inspection unit 23 are controlled based on the information on the areas set in the inspecting mode determining step and stored in the area memory 26 as areas to undergo the chip comparing inspection and the areas to undergo the cell comparing inspection. Both the cell comparing inspection and the chip comparing inspection are performed for the repetitive pattern areas 133 and 134, while only the chip comparing inspection is performed for the random pattern area 132.

In the pattern inspecting step, the chip comparing inspection unit 21 performs the chip comparing inspection for the random pattern area 132 and repetitive pattern areas 133 and 134. The chip comparing inspection unit 21 inspects for defects by successively comparing images of patterns in certain areas on an immediately preceding chip 131 acquired with the camera 15 and stored in the image memory 22, and images of patterns in the corresponding areas on the current chip 131 acquired with the camera 15.

The construction and inspecting process of the chip comparing inspection unit 21 will be described in detail hereinafter.

In the pattern inspecting step, the repetitive pattern areas 133 and 134 undergo also the cell comparing inspection by the cell comparing inspection unit 23. The cell comparing inspection unit 23 inspects for defects by successively comparing images of patterns in certain areas on the immediately preceding chip 131 acquired with the camera 15 and stored in the image memory 24, and images of patterns in the corresponding areas on the current chip 131 acquired with the camera 15.

When a relatively large defect is present in the repetitive pattern areas 133 and 134, as shown in FIG. 16, the defect cannot be detected in the cell comparing inspection by the cell comparing inspection unit 23. However, such a relatively large defect is detected in the chip comparing inspection by the chip comparing inspection unit 21. Such a relatively large defect can be reliably detected, without misdetection, in the chip comparing inspection though requiring a relatively large error allowance.

The above chip comparing inspection and cell comparing inspection are carried out for an entire area defining chips 131 on the surface of wafer W. This is achieved by operating the table driver 14 to drive the substrate support table 11 through the actuators 12 and 13, thereby moving the wafer W supported thereon relative to the camera 15.

Subsequently, the integrating decision unit 25 integrates results of the inspection by the chip comparing inspection unit 21 and results of inspection by the cell comparing inspection unit 23, and provides results of the inspection for all the chips formed on the wafer W. It is to be noted that the integrating decision unit 25 performs the result integration based on OR operations of the results of the inspection by the chip comparing inspection unit 21 and the results of inspection by the cell comparing inspection unit 23.

The results of the inspection are displayed on the CRT 19 through the controller 17.

As described above, the pattern inspecting apparatus in this embodiment performs both the cell comparing inspection and the chip comparing inspection for the repetitive pattern areas 133 and 134, and the chip comparing inspection for the random pattern area 132. This realizes an accurate detection of even a relatively large defect present in the repetitive pattern areas 133 and 134.

In the above embodiment, the area setting step is executed to set the random pattern area 132 with random patterns formed therein, as well as the repetitive pattern areas 133 and 134 with repetitive patterns formed therein. Instead, only the repetitive pattern areas 133 and 134 may be set, leaving all the other areas to be regarded as random pattern areas. In this case, the chip comparing inspection is carried out for all areas on each chip 131, and then the cell comparing inspection is carried out for the repetitive pattern areas 133 and 134 of the chip 131.

The specific construction of the chip comparing inspection unit 21 of the above pattern inspecting apparatus and its inspecting process for comparing and inspecting chips will be described next.

Figure 5:
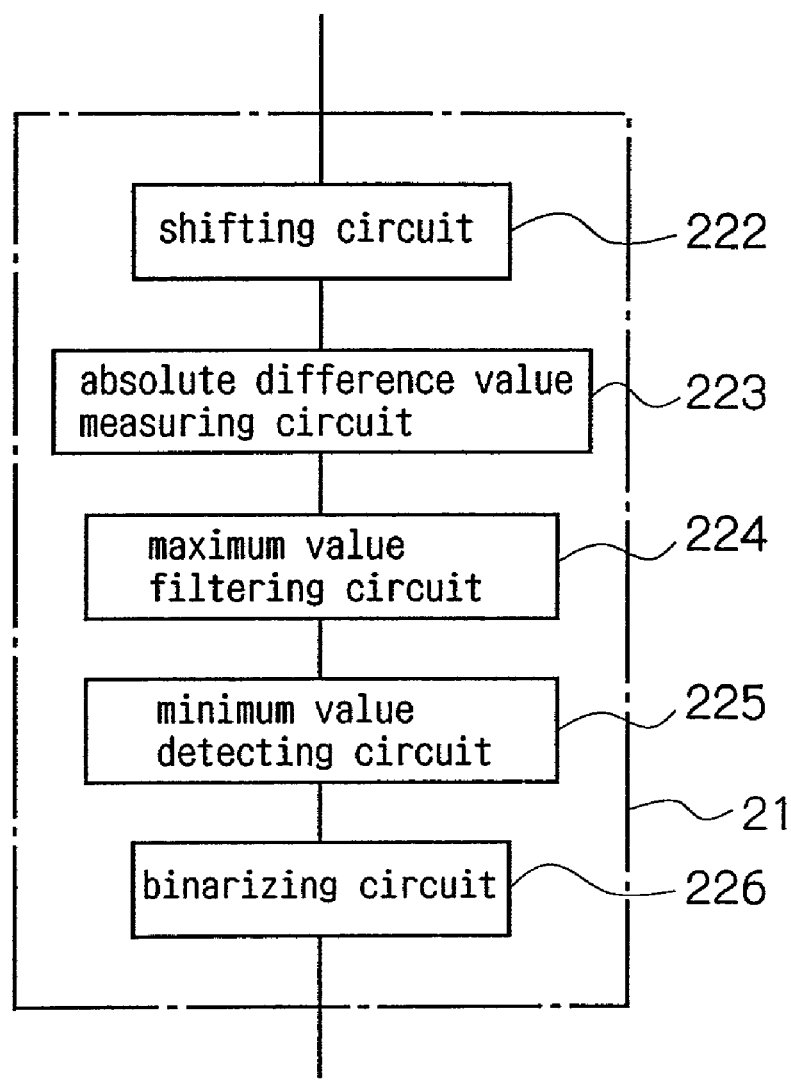
FIG. 5 is a block diagram of a chip comparing inspection unit.

FIG. 5 is a block diagram of the chip comparing inspection unit 21.

The chip comparing inspection unit 21 includes a shifting circuit 222 for shifting a reference image stored in the image memory 22 shown in FIG. 1, by a fixed amount two-dimensionally in peripheral directions relative to an image read with the camera 15 to be inspected, an absolute difference value measuring circuit 223 for measuring an absolute value of a difference between the reference image in each shift position and the image under inspection, thereby to obtain an absolute difference value image for each shift position, a maximum value filtering circuit 224 for performing a maximum value filtering process on the absolute difference value image for each shift position, thereby to obtain a maximum value image for each shift position, a minimum value detecting circuit 225 for detecting a minimum value among pixel values of corresponding positions in the maximum value images, thereby to obtain a defect image, and a binarizing circuit 226 for binarizing the defect image by a fixed threshold to identify a defect.

The above reference image stored in the memory 22 is a pattern image of a certain area of an immediately preceding chip 131 photographed with the camera 15 and stored in the image memory 21. Instead of this pattern image, the apparatus may use a reference image photographed with the camera 15 and stored in the image memory 21 to serve as a master pattern.

Figure 6:
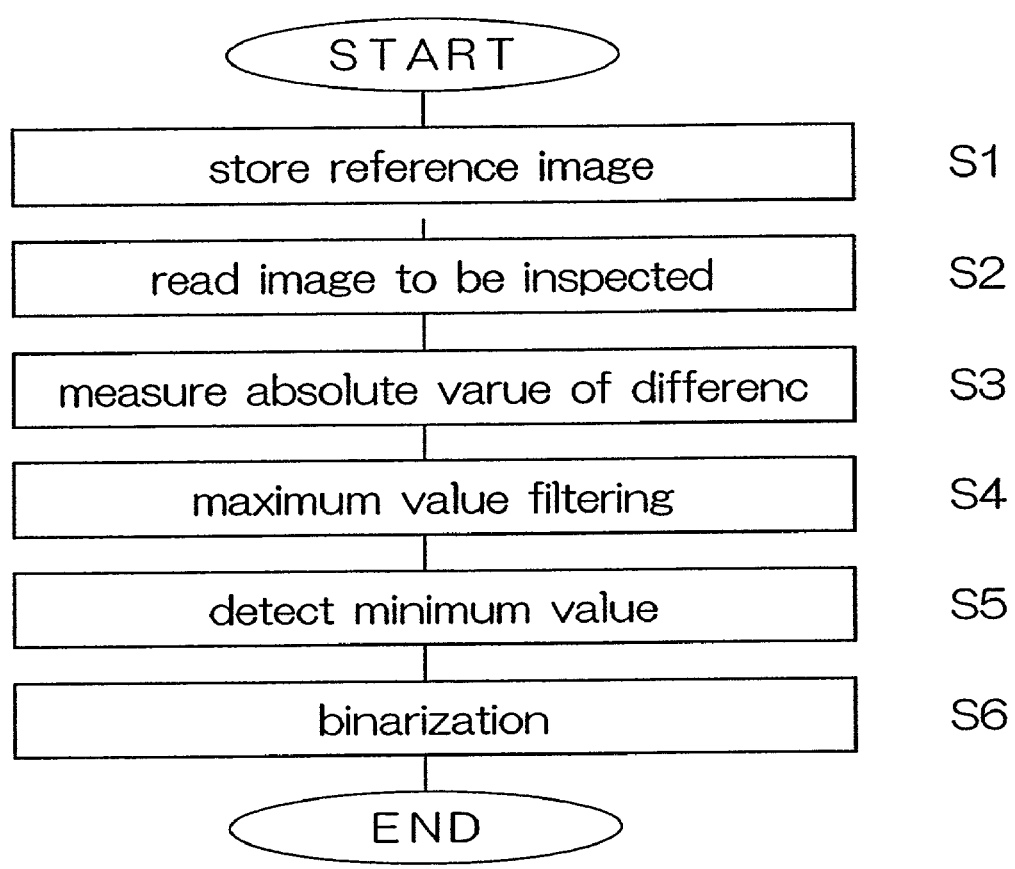
FIG. 6 is a flow chart of a chip comparing inspection process.

FIG. 6 is a flow chart of the inspecting process carried out by the chip comparing inspection unit 21 for comparing and inspecting chips.

For performing the chip comparing inspection, a reference image is stored beforehand in the image memory 22 shown in FIG. 1 (step S1). In this reference image storing step, a pattern image of a certain area of an immediately preceding chip is read with the camera 15 as a continuous tone image, and its image data is stored in the image memory 22.

Next, an image to be subjected to the chip comparing inspection is read with the camera 15 as a continuous tone image (step S2). The image read in this image-for-inspection reading step is transmitted to the absolute difference value measuring circuit 223. The image to be inspected may once be stored in the image memory 22.

FIG. 7 is a schematic view of a reference image 31 stored in the image memory 22 and an image 32 read with the camera 15 to be inspected.

In this embodiment, as seen from FIG. 7, the reference image 31 includes 18×18 pixels while the image 32 to be inspected includes 16×16 pixels. The reference image 31 is assumed here to include a defect or pattern 33 corresponding to four pixels.

Next, the reference image 31 stored in the reference image storing step is shifted by an amount corresponding to one pixel two-dimensionally in peripheral directions relative to the image 32 read in the image-for-inspection reading step. Then, an absolute value of a difference between the reference image 31 and the image 32 under inspection is measured for each shift position (step S3).

In this absolute difference value measuring step, the shifting circuit 222 sets the reference image 31 and the image 32 under inspection to nine positions as shown in FIG. 8. Specifically, these positions are a position where the upper side and left side of the reference image 31 register with the upper side and left side of the image 32 under inspection, a position where only the upper side of the reference image 31 registers with the upper side of the image 32 under inspection, a position where the upper side and right side of the reference image 31 register with the upper side and right side of the image 32 under inspection, a position where only the left side of the reference image 31 registers with the left side of the image 32 under inspection, a position where none of the sides of the reference image 31 register with the corresponding sides of the image 32 under inspection, a position where only the right side of the reference image 31 registers with the right side of the image 32 under inspection, a position where the left side and lower side of the reference image 31 register with the left side and lower side of the image 32 under inspection, a position where only the lower side of the reference image 31 registers with the lower side of the image 32 under inspection, and a position where the right side and lower side of the reference image 31 register with the right side and lower side of the image 32 under inspection.

The absolute difference value measuring circuit 223 obtains an absolute difference value image for each of these nine shift positions by comparing the reference image 31 stored in the reference image storing step and the image 32 read in the image-for-inspection reading step, with the two images arranged in the shift positions. FIG. 8 shows nine absolute difference value images 34a–34i thus obtained.

In this embodiment, the reference image 31 is shifted by an amount corresponding to one pixel two-dimensionally relative to the image 32 under inspection to provide the nine shift positions. However, the amount of shift need not correspond to one pixel. Where the amount of shift corresponds to two pixels, for example, 25 shift positions are provided. Where the amount of shift corresponds to n pixels, the number of shift positions thereby provided will be (2n+1)×(2n+1).

The amount of shift need not necessarily correspond to a multiple of the pixels, but may be a unit less than one pixel as described in Japanese Patent Publication (Unexamined) No. 2000-028333, for example.

In this embodiment, the reference image 31 and image 32 under inspection are continuous tone images. Where binary images are used instead, the absolute difference value measurement step is executed to perform an exclusive-OR operation on the reference image 31 in each shift position and image 32 under inspection.

Figure 9:
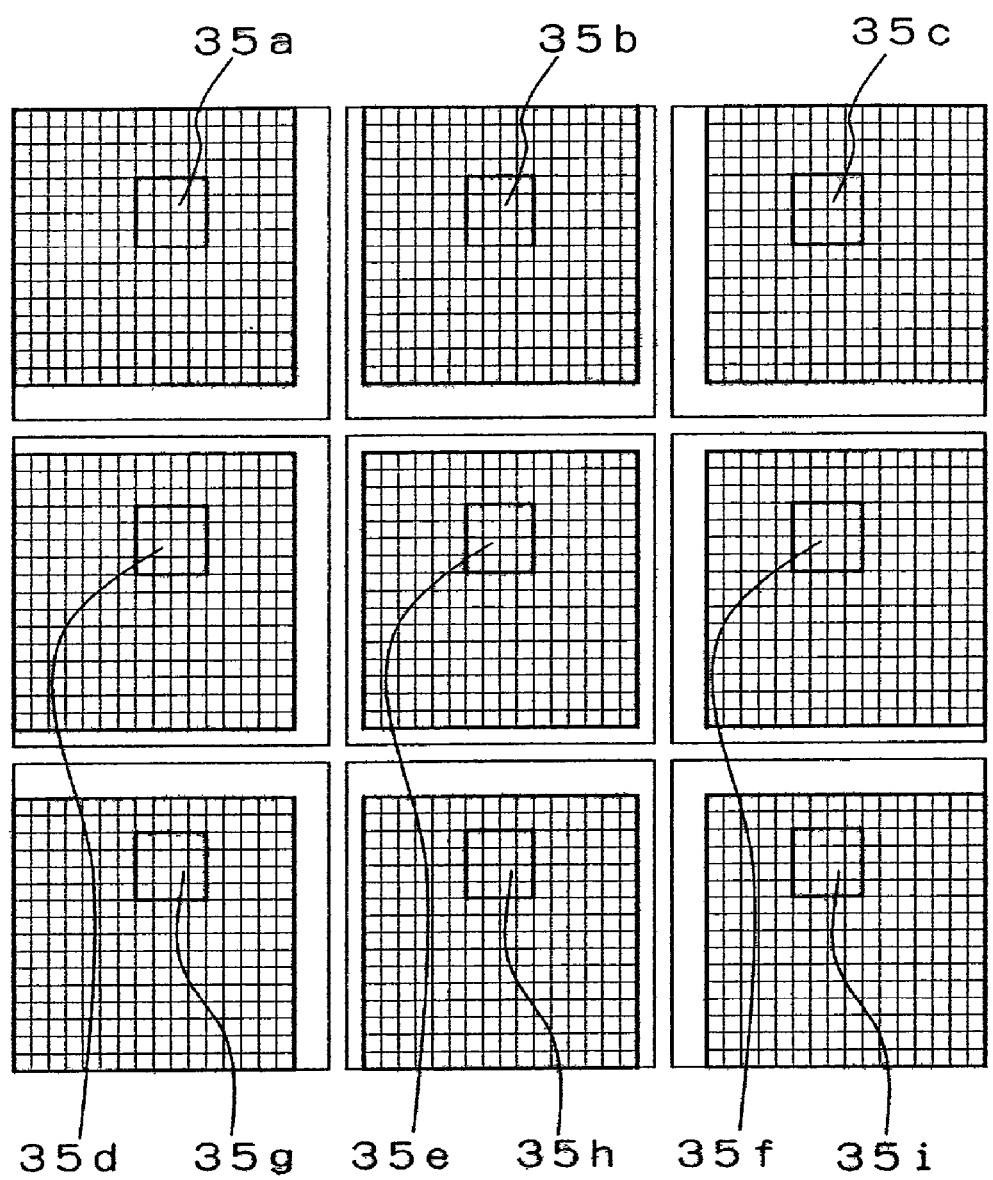
FIG. 9 is a schematic view of maximum difference value images.

Referring again to FIG. 6, a maximum value filtering process (expansion process) is executed on the absolute difference value images 34a–34i for the respective shift positions obtained in the absolute difference value measuring step (step S4). In this maximum value filtering step where, for example, each pixel of the absolute value images 34a–34i is placed in each position of a maximum value filter area of three rows by three columns, a maximum value image is obtained for each shift position by setting a maximum value of the image in the maximum value filter area as a value of its center. FIG. 9 shows nine maximum difference value images 35a–35i thus obtained.

In the above description, the maximum value filtering process employs a 3×3 window, but a larger, N×N window may be used. In this case, the value of N should be 2n+1 or more where n is an amount of shift as noted hereinbefore.

A window other than rectangular, such as a circular window, may be used as long as it is in vertical and left-right symmetry. Where a circular window is used, the window is shifted in a circle. In this case, the diameter of the circular window corresponds to N noted above where n is the amount of shift of the circular window.

Next, a minimum value is detected among pixel values of corresponding positions in the maximum value images 35a–35i obtained for the respective shift positions in the maximum value filtering step (step S5). This minimum value detecting step is executed to obtain a defect image by selecting a minimum value from among pixel values of corresponding positions in the nine maximum difference value images 35a–35i corresponding to the respective shift positions. FIG. 10 shows a defect image 36 thus obtained.

As shown in FIGS. 7(a) and 10, the defect image 36 detected is the same size as the defect or pattern 33 in the reference image 31. That is, where the chip comparing inspection unit 21 is used under the above condition, in which the amount of shift is n, and the size of the maximum value filter is [2n+1]×[2n+1], the defect image 36 of the same size as the defect size may be obtained.

Referring again to FIG. 6, final defect information is obtained by binarizing this defect image 36 with a predetermined threshold (step S6).

In the above description, the binarizing step is executed after the minimum value detecting step (step S5). However, the binarizing step may be executed immediately following the absolute difference value measuring step (step S3). In this case, the maximum value filtering step (step S4) sets "1" to the center provided that "1" exists anywhere inside the maximum value filter area. The minimum value detecting step (step S5) performs an AND operation on the maximum value images for the respective shift positions.

In the embodiment illustrated in FIGS. 7 through 10, the reference image 31 includes a defect 33 corresponding to four pixels, or the reference image 31 includes a pattern 33 corresponding to four pixels but no such pattern is found in the image 32 under inspection. However, where the image under inspection includes a defect, the chip comparing inspection unit 21 in this embodiment is capable of detecting this defect through the same process.

FIG. 11 is a schematic view of a reference image 41 stored in the image memory 22 in the reference image storing step (step 1) and an image 42 to be inspected which is read with the camera 15 in the image-for-inspection reading step (step S2).

In this embodiment, as seen from FIG. 11, the image 42 to be inspected includes a defect or pattern 43 corresponding to four pixels.

Figure 12:
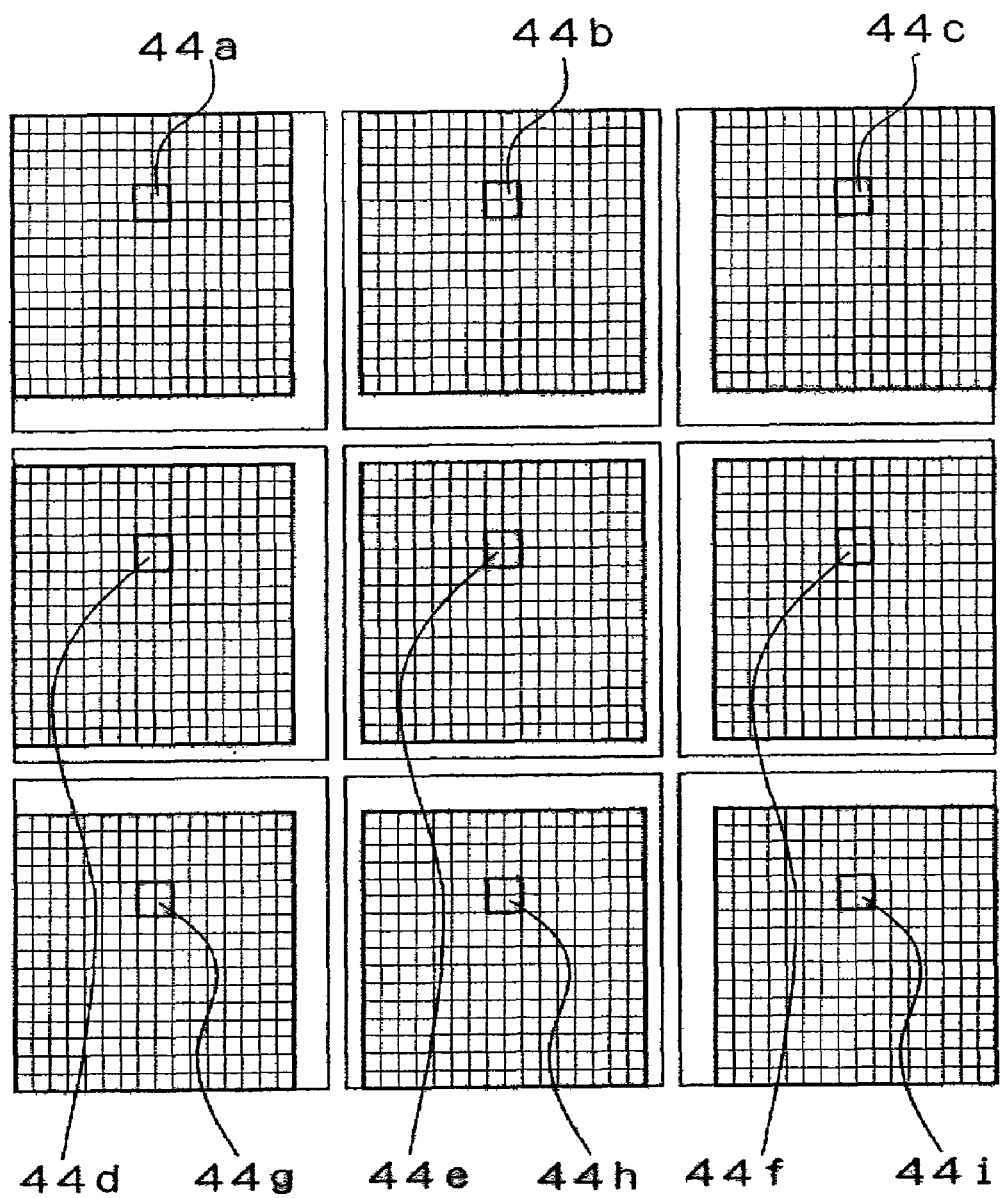
FIG. 12 is a schematic view of absolute value images.

Under such a condition, nine absolute difference value images 44a–44i as shown in FIG. 12 are obtained by executing the absolute difference value measuring step (step S3) in which the reference image 41 is shifted by an amount corresponding to one pixel two-dimensionally in peripheral directions relative to the image 42 under inspection, and then an absolute value of a difference between the reference image 41 and the image 42 under inspection is measured for each shift position. These absolute value images 44a–44i differ from the absolute value images 34a–34i shown in FIG. 8, in that the absolute value images 44a–44i are all in the same position.

Figure 13:
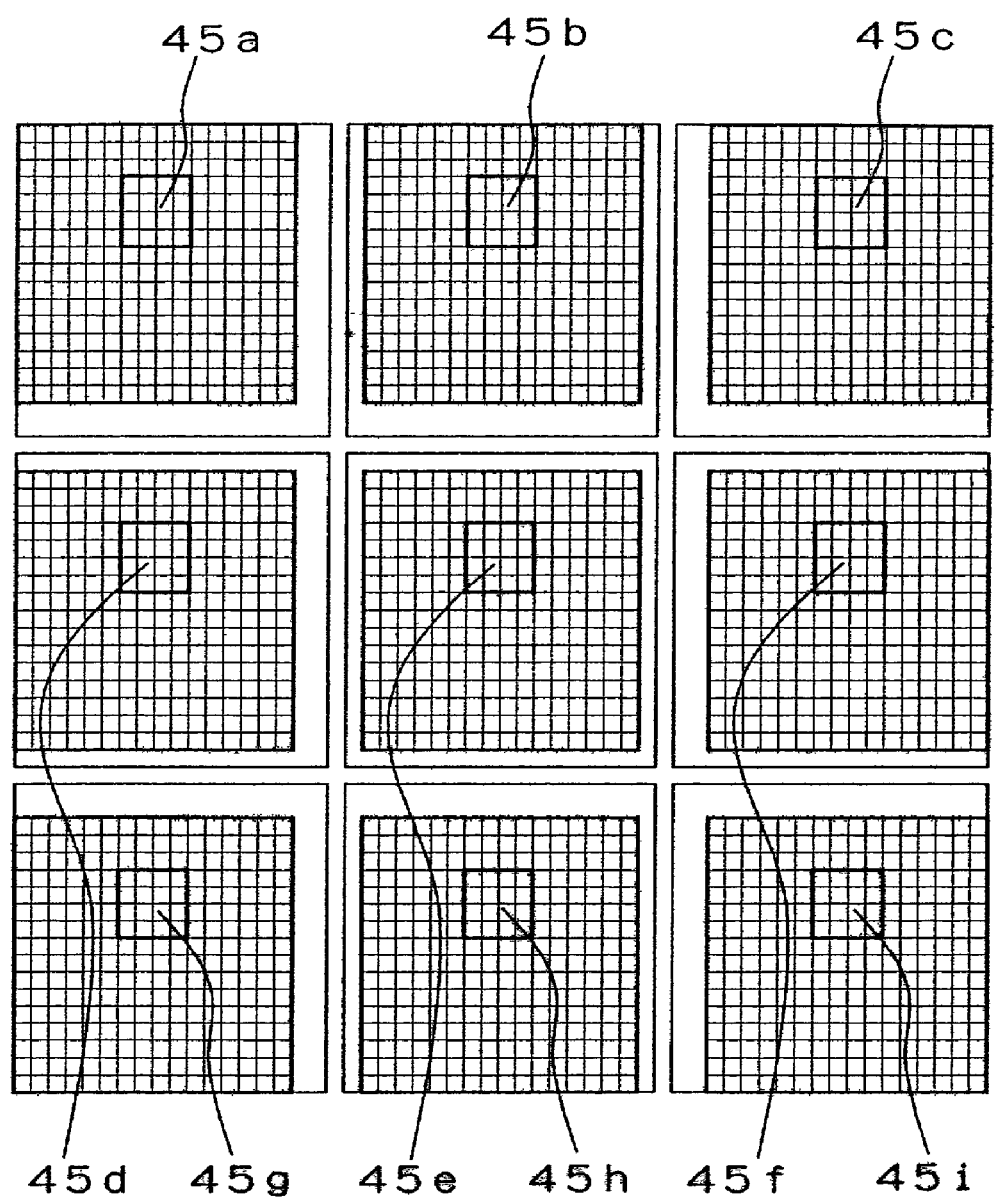
FIG. 13 is a schematic view of maximum difference value images.

These absolute difference value images 44a–44i are subjected to the 3×3 maximum value filtering process (step S4) to obtain nine maximum difference value images 45a–45i as shown in FIG. 13.

Figure 14:
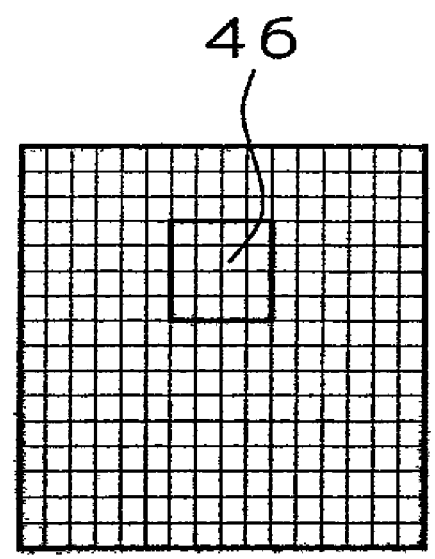
FIG. 14 is a schematic view of a defect image.
Figure 15:
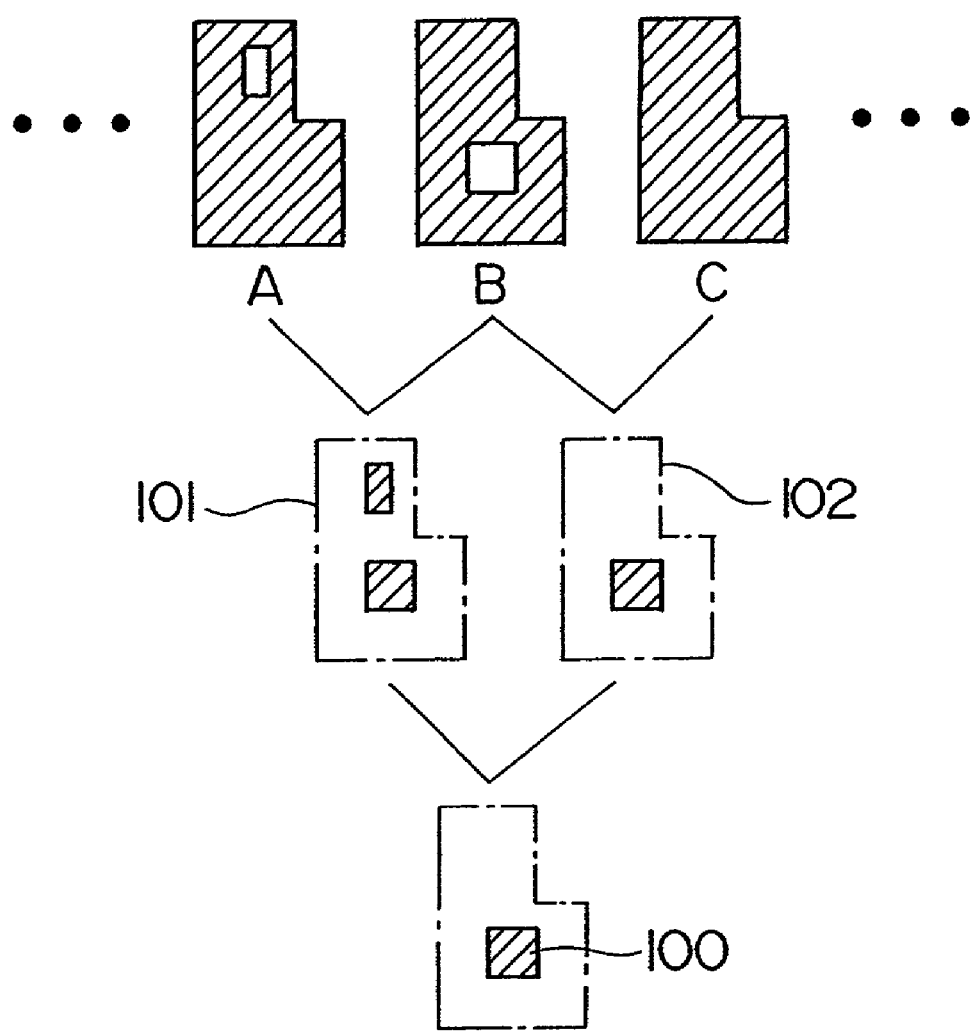
FIG. 15 is an explanatory view illustrating an operation for detecting a defect by using a cell comparing inspection.

Subsequently, a minimum value is detected among pixel values of corresponding positions in the maximum value images 45a–45i (step S5) to obtain a defect image 46 as shown in FIG. 14.

As shown in FIGS. 11(b) and 14, the defect image 46 detected has a size corresponding to the defect 43 in the image 42 under inspection as expanded by the size of the maximum value filter. That is, where the chip comparing inspection unit 21 is used under the above condition, in which the amount of shift is n, and the size of the maximum value filter is [2n+1]×[2n+1], the defect image 46 of the size corresponding to the defect size expanded by the size of the maximum value filter may be obtained.

Finally, referring to FIG. 6, final defect information is obtained by binarizing this defect image 46 with the predetermined threshold (step S6).

The present invention may be embodied in other specific forms without departing from the spirit or essential attributes thereof and, accordingly, reference should be made to the appended claims, rather than to the foregoing specification, as indicating the scope of the invention.

The present application claims priority benefit under 35 U.S.C. Section 119 of Japanese Patent Applications Nos. 2001-112538 and 2001-112539 filed in the Japanese Patent Office on Apr. 11, 2001, the entire disclosure of which is incorporated herein by reference.

What is claimed is:

1. A pattern inspecting apparatus for inspecting patterns in numerous chips formed on a substrate, comprising:
   a substrate support for supporting said substrate;
   a camera for acquiring images of said chips;
   moving means for moving said substrate support and said camera relative to each other;
   an image memory for storing the images of said chips acquired by said camera;
   an area setting mechanism for setting a repetitive pattern area having repetitive patterns formed therein, and a random pattern area having random patterns formed therein, to each of said chips whose images are acquired by said camera;
   an area memory for storing said repetitive pattern area and said random pattern area;
   a cell comparing inspection unit for executing a cell comparison to detect a pattern defect by comparing the repetitive patterns in said repetitive pattern area set to each of said chips and stored in said area memory; and
   a chip comparing inspection unit for executing a chip comparison to detect a pattern defect by comparing corresponding patterns in said repetitive pattern area and said random pattern area set to said chips and stored in said area memory.

2. A pattern inspecting apparatus as defined in claim 1, wherein said chip comparing inspection unit includes:
   a shifting circuit for shifting a reference image stored in said image memory, to shift positions displaced by a fixed amount two-dimensionally in peripheral directions relative to an image read by said camera to be inspected;
   an absolute difference value measuring circuit for measuring an absolute value of a difference between said reference image in each of said shift positions and said inspected image, thereby to obtain absolute difference value images for said shift positions;
   a maximum value filtering circuit for performing a maximum value filtering process on said absolute difference value images for said shift positions, thereby to obtain maximum value images for said shift positions; and
   a minimum value detecting circuit for detecting a minimum value among pixel values of corresponding positions in said maximum value images, thereby to obtain a defect image.

3. An inspecting apparatus for inspecting repetitive patterns in repetitive pattern areas of numerous chips formed on a substrate,
   characterized in that a pattern defect is detected by executing a cell comparison for comparing said repetitive patterns in each of said repetitive pattern areas of said chips, and a chip comparison for comparing corresponding patterns in said repetitive pattern areas of said chips.

4. A pattern inspecting method for inspecting patterns in numerous chips formed on a substrate, comprising:
   an area setting step for setting a repetitive pattern area having repetitive patterns formed therein, and a random pattern area having random patterns formed therein to each of said chips; and
   a defect detecting step for executing both a cell comparison to detect a pattern defect by comparing the repetitive patterns in said repetitive pattern area set to each of said chips, and a chip comparison to detect a pattern defect by comparing corresponding patterns in said repetitive pattern area set to said chips, and executing the chip comparison to detect a pattern defect by comparing corresponding patterns in said random pattern area set to said chips.

5. A pattern inspecting method as defined in claim 4, wherein said area setting step is executed for setting a repetitive pattern area having repetitive patterns formed therein, and a random pattern area having random patterns formed therein, by photographing the patterns on each of said chips, displaying the patterns in enlargement on a display device, and referring to the patterns displayed in enlargement.

6. A pattern inspecting method as defined in claim 4, wherein said chip comparison executed in said defect detecting step includes:

a reference image storing step for storing a reference image;

an image-for-inspection reading step for reading an image to be inspected;

an absolute difference value measuring step for shifting said reference image to shift positions displaced by a fixed amount two-dimensionally in peripheral directions relative to said image to be inspected, and measuring an absolute value of a difference between said reference image in each of said shift positions and said image to be inspected, thereby to obtain absolute difference value images for said shift positions;

a maximum value filtering step for performing a maximum value filtering process on said absolute difference value images for said shift positions, thereby to obtain maximum value images for said shift positions; and a minimum value detecting step for detecting a minimum value among pixel values of corresponding positions in said maximum value images, thereby to obtain a defect image.

7. A pattern inspecting method as defined in claim 6, wherein said reference image and said image to be inspected are continuous tone images, said minimum value detecting step being followed by a binarizing step for binarizing said defect image.

8. A pattern inspecting method as defined in claim 6, wherein said reference image and said image to be inspected are continuous tone images, said absolute difference value measuring step being followed by a binarizing step for binarizing said absolute difference value images.

\* \* \* \* \*